(12) United States Patent
Stevens

(10) Patent No.: US 8,898,848 B1
(45) Date of Patent: Dec. 2, 2014

(54) SKIN CLEANSING FINGER SLEEVE AND ASSOCIATED USE THEREOF

(76) Inventor: Kasia E. Stevens, Harrison, NY (US)

( * ) Notice: Subject to any disclaimer, the term of this patent is extended or adjusted under 35 U.S.C. 154(b) by 99 days.

(21) Appl. No.: 13/619,136

(22) Filed: Sep. 14, 2012

Related U.S. Application Data

(60) Provisional application No. 61/535,030, filed on Sep. 15, 2011.

(51) Int. Cl.
*A47L 13/19* (2006.01)

(52) U.S. Cl.
USPC .............................. 15/104.94; 15/277; 2/163

(58) Field of Classification Search
CPC ............ A47L 13/17–13/19; A46B 2200/1046; A61Q 1/12; A61Q 1/14
USPC .......... 15/104.93, 104.94, 227; 604/289–290; 510/295; 2/163
See application file for complete search history.

(56) References Cited

U.S. PATENT DOCUMENTS

| | | | | | |
|---|---|---|---|---|---|
| 1,836,833 | A | * | 12/1931 | Ames ......................... | 15/104.94 |
| 4,347,931 | A | * | 9/1982 | Ginger et al. ................ | 206/438 |
| 5,320,531 | A | | 6/1994 | Delizo-Madamba | |
| 5,577,272 | A | | 11/1996 | Fisher | |
| 6,119,038 | A | * | 9/2000 | Cook ................... | 607/3 |
| 6,647,549 | B2 | * | 11/2003 | McDevitt et al. ................... | 2/21 |
| 7,012,169 | B2 | | 3/2006 | McDevitt et al. | |
| 2006/0247585 | A1 | * | 11/2006 | Kelly ............................ | 604/290 |
| 2007/0067932 | A1 | * | 3/2007 | Young et al. ................ | 15/104.94 |

* cited by examiner

*Primary Examiner* — Laura C Guidotti

(57) ABSTRACT

A disposable skin cleansing finger sleeve cleans and maintains a clean face, removes facial make up, and applies medicine to the face in the treatment of skin conditions. The skin cleansing finger sleeve includes an elongated body formed from water impermeable material wherein the body has an open proximal end and a closed distal end capable of being removably positioned about a user finger. A viscous skin cleansing agent may be pre-applied (impregnate, coated, soaked, etc.) or applied after-the-fact (applied by the user) to the body for treating the user skin. Advantageously, the finger sleeve is capable of cleaning a user face by applying the skin cleansing agent to the user face and removing facial makeup therefrom.

11 Claims, 3 Drawing Sheets

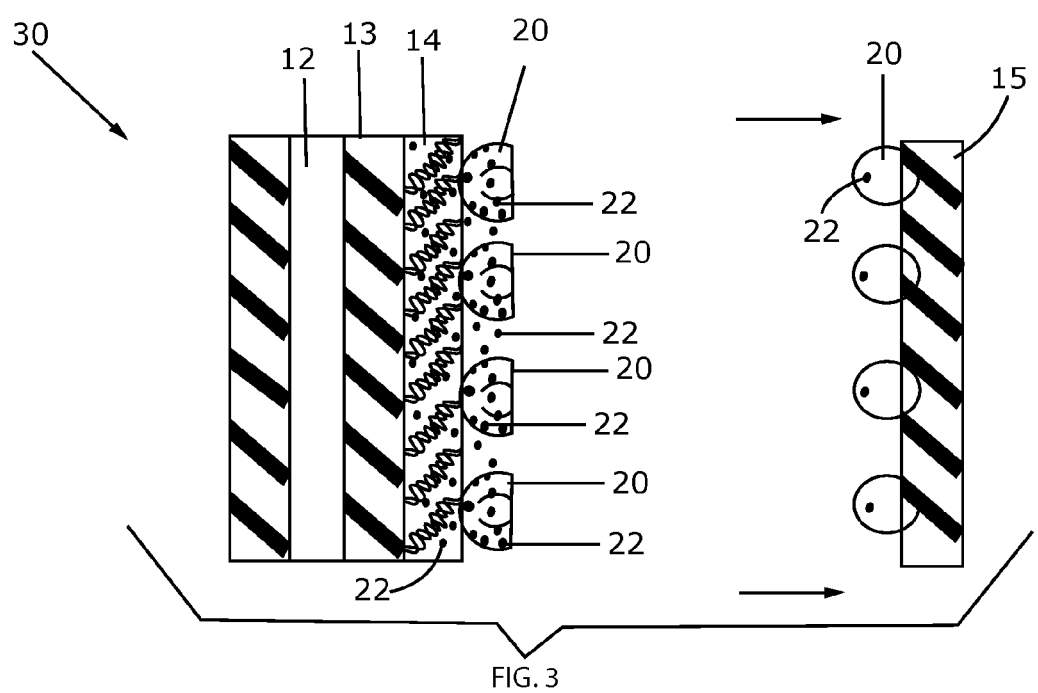

SKIN CLEANSING FINGER SLEEVE AND ASSOCIATED USE THEREOF

CROSS REFERENCE TO RELATED APPLICATIONS

This application claims the benefit of U.S. Provisional Application No. 61/535,030 filed Sep. 15, 2011, the entire disclosures of which are incorporated herein by reference.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND OF NON-LIMITING EXEMPLARY EMBODIMENT(S) OF THE PRESENT DISCLOSURE

1. Technical Field

This non-limiting exemplary embodiment(s) relates to skin cleansing products and, more particularly, to a disposable skin cleansing finger sleeve to clean and maintain a clean face, remove facial make up, and apply medicine to the face in the treatment of skin conditions.

2. Prior Art

Millions of consumers suffer from various forms of acne. The most common skin disease treated by physicians, acne is a chronic condition that affects approximately 85 percent of adolescents and young adults. An eruptive skin disease, acne most often occurs on the face, neck and back and is primarily a disorder of the sebaceous follicles of the skin. The natural secretion or these follicles (sebum) accumulates in the skin, mixing with dirt, dust and perspiration, inflaming the tissue and resulting in blackheads and pimples. Not surprisingly, blackheads and pimples can detract from one's overall appearance and can cause embarrassment and discomfort to the sufferer of these symptoms. As such, achieving clear skin is a goal for anyone who is conscientious about their appearance.

Accordingly, a need remains for a disposable skin cleansing finger sleeve in order to overcome prior art shortcomings. The present invention satisfies such a need by providing a disposable skin cleansing finger sleeve containing a cleansing solution that is convenient and easy to use, lightweight yet durable in design, versatile in its applications, and designed for cleaning pores, as well as eliminating blackheads and acne and applying medicine. Also, the finger sleeve can be a device for women to use for makeup removal. The finger sleeve in its application to the face, will effectively remove facial make up.

BRIEF SUMMARY OF NON-LIMITING EXEMPLARY EMBODIMENT(S) OF THE PRESENT DISCLOSURE

In view of the foregoing background, it is therefore an object of the non-limiting exemplary embodiment(s) to provide a disposable skin cleansing finger sleeve to clean and maintain a clean face, remove facial make up, and apply medicine to the face in the treatment of skin conditions. These and other objects, features, and advantages of the non-limiting exemplary embodiment(s) are provided by a skin cleansing finger sleeve including an elongated body formed from water impermeable material wherein the body has an open proximal end and a closed distal end capable of being removably positioned about a user finger. A viscous skin cleansing agent may be pre-applied (impregnate, coated, soaked, etc.) or applied after-the-fact (applied by the user) to the body for treating the user skin. Advantageously, the finger sleeve is capable of cleaning a user face by applying the skin cleansing agent to the user face and removing facial makeup therefrom.

In a non-limiting exemplary embodiment, the body includes an abrasive outer surface having a plurality of female protrusions extending outwardly therefrom wherein the skin cleansing agent is housed within the female protrusions. A protective layer is also provided and has a plurality of male protrusions extending outwardly therefrom.

In a non-limiting exemplary embodiment, when the protective layer is affixed to the outer surface of the body, the male protrusions are interfitted within the female protrusions thereby maintaining the skin cleansing agent compartmentalized entirely within the female protrusions.

In a non-limiting exemplary embodiment, when the protective layer is removed from the outer surface of the body, the male protrusions are detached from the female protrusions thereby causing the skin cleansing agent to egress outwardly from the female protrusions and spread along the outer surface of the body.

In a non-limiting exemplary embodiment, the cleansing agent includes a liquid hypo-allergenic solution.

In a non-limiting exemplary embodiment, the female protrusions include spherical sockets and the male protrusions include spherical balls.

In a non-limiting exemplary embodiment, a jar is provided which contains the cleansing agent therein.

In a non-limiting exemplary embodiment, the outer surface is smooth and the cleansing agent is disposed along the outer surface of the finger sleeve.

The disclosure further includes a method of utilizing a skin cleansing finger sleeve. Such a method includes the chronological steps of: providing an elongated body formed from water impermeable material wherein the body has an open proximal end and a closed distal end; providing and applying a viscous skin cleansing agent to the body for treating the user skin; removably positioning the body about a user finger; and the finger sleeve cleaning a user face by applying the skin cleansing agent to the user face and removing facial makeup.

There has thus been outlined, rather broadly, the more important features of non-limiting exemplary embodiment(s) of the present disclosure so that the following detailed description may be better understood, and that the present contribution to the relevant art(s) may be better appreciated. There are additional features of the non-limiting exemplary embodiment(s) of the present disclosure that will be described hereinafter and which will form the subject matter of the claims appended hereto.

BRIEF DESCRIPTION OF THE NON-LIMITING EXEMPLARY DRAWINGS

The novel features believed to be characteristic of non-limiting exemplary embodiment(s) of the present disclosure are set forth with particularity in the appended claims. The non-limiting exemplary embodiment(s) of the present disclosure itself, however, both as to its organization and method of operation, together with further objects and advantages thereof, may best be understood by reference to the following description taken in connection with the accompanying drawings in which:

FIG. 3 is a cross-sectional view wherein the protective layer has been peeled away from the outer surface of the finger sleeve thereby exposing the skin cleansing agent by extracting the male protrusions from the female protrusions.

Figure 1:
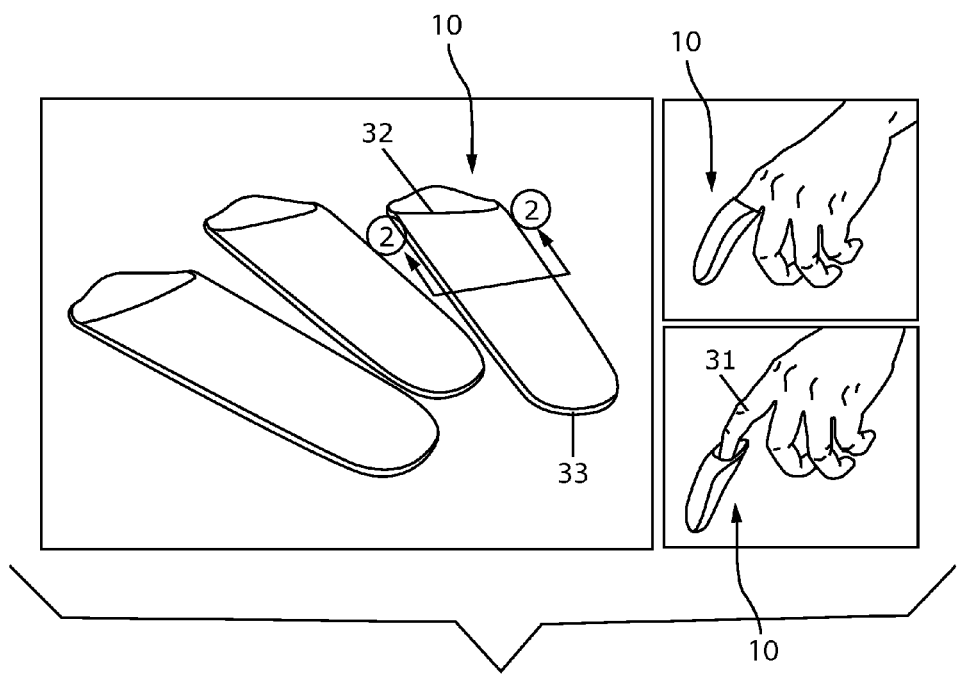
FIG. 1 is a perspective view showing a skin cleansing finger sleeve being positioned on a user finger, in accordance with the non-limiting exemplary embodiment(s)

Those skilled in the art will appreciate that the figures are not intended to be drawn to any particular scale; nor are the figures intended to illustrate every non-limiting exemplary embodiment(s) of the present disclosure. The present disclosure is not limited to any particular non-limiting exemplary embodiment(s) depicted in the figures nor the shapes, relative sizes or proportions shown in the figures.

DETAILED DESCRIPTION OF NON-LIMITING EXEMPLARY EMBODIMENT(S) OF THE PRESENT DISCLOSURE

The present disclosure will now be described more fully hereinafter with reference to the accompanying drawings, in which non-limiting exemplary embodiment(s) of the present disclosure is shown. The present disclosure may, however, be embodied in many different forms and should not be construed as limited to the non-limiting exemplary embodiment(s) set forth herein. Rather, such non-limiting exemplary embodiment(s) are provided so that this application will be thorough and complete, and will fully convey the true spirit and scope of the present disclosure to those skilled in the relevant art(s). Like numbers refer to like elements throughout the figures.

The illustrations of the non-limiting exemplary embodiment(s) described herein are intended to provide a general understanding of the structure of the present disclosure. The illustrations are not intended to serve as a complete description of all of the elements and features of the structures, systems and/or methods described herein. Other non-limiting exemplary embodiment(s) may be apparent to those of ordinary skill in the relevant art(s) upon reviewing the disclosure. Other non-limiting exemplary embodiment(s) may be utilized and derived from the disclosure such that structural, logical substitutions and changes may be made without departing from the true spirit and scope of the present disclosure. Additionally, the illustrations are merely representational are to be regarded as illustrative rather than restrictive.

One or more embodiment(s) of the disclosure may be referred to herein, individually and/or collectively, by the term "non-limiting exemplary embodiment(s)" merely for convenience and without intending to voluntarily limit the true spirit and scope of this application to any particular non-limiting exemplary embodiment(s) or inventive concept. Moreover, although specific embodiment(s) have been illustrated and described herein, it should be appreciated that any subsequent arrangement designed to achieve the same or similar purpose may be substituted for the specific embodiment(s) shown. This disclosure is intended to cover any and all subsequent adaptations or variations of other embodiment(s). Combinations of the above embodiment(s), and other embodiment(s) not specifically described herein, will be apparent to those of skill in the relevant art(s) upon reviewing the description.

References in the specification to "one embodiment(s)", "an embodiment(s)", "a preferred embodiment(s)", "an alternative embodiment(s)" and similar phrases mean that a particular feature, structure, or characteristic described in connection with the embodiment(s) is included in at least an embodiment(s) of the non-limiting exemplary embodiment(s). The appearances of the phrase "non-limiting exemplary embodiment" in various places in the specification are not necessarily all meant to refer to the same embodiment(s).

Figure 2:
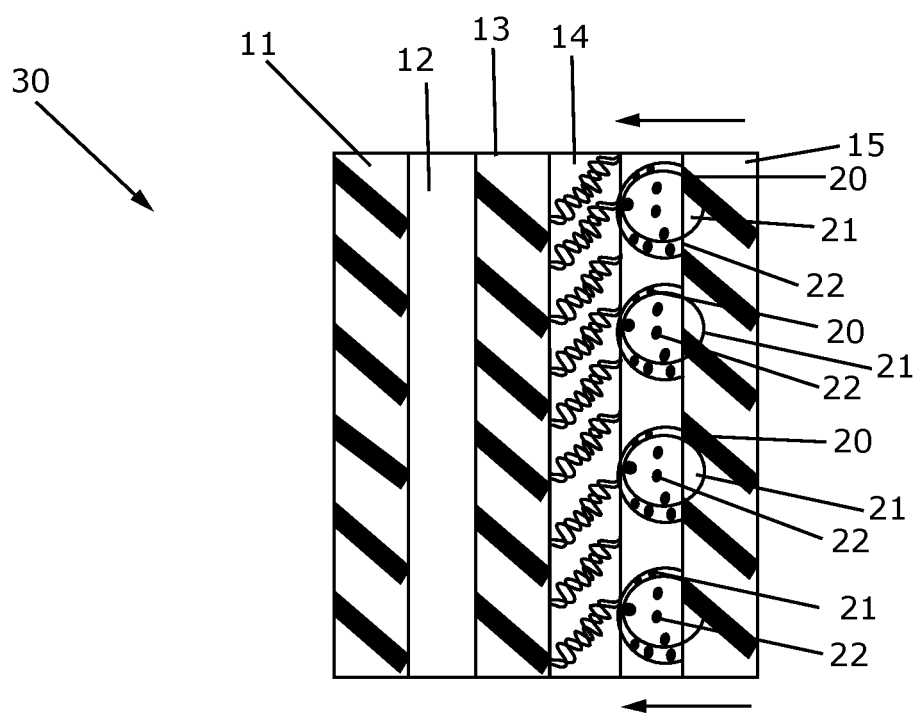
FIG. 2 is a cross-sectional view taken along line 2-2 wherein the protective layer is affixed to the outer surface.

The non-limiting exemplary embodiment(s) is/are referred to generally in FIGS. 1-3 and is/are intended to provide a disposable skin cleansing finger sleeve to clean and maintain a clean face, remove facial make up, and apply medicine to the face in the treatment of skin conditions. It should be understood that such non-limiting exemplary embodiment(s) may be used to treat many different types of skin conditions, and should not be limited to the uses described herein.

The skin cleansing finger 31 sleeve 10 includes an elongated body 30 formed from water impermeable material wherein the body 30 has an open proximal end 32 and a closed distal end 33 capable of being removably positioned about a user finger 31. A viscous skin cleansing agent 22 may be pre-applied (impregnate, coated, soaked, etc.) or applied after-the-fact (applied by the user) to the body 30 for treating the user skin. Advantageously, the finger 31 sleeve 10 is capable of cleaning a user face by applying the skin cleansing agent 22 to the user face and removing facial makeup therefrom.

In a non-limiting exemplary embodiment, the body 30 includes anterior and posterior surfaces 11, 13 defining a cavity 12 therebetween for receiving the user finger 31. The anterior and posterior surfaces 11, 13 are preferably formed from water impermeable material for shield the user finger 31 from undesirably liquid and debris. An abrasive outer surface 14 directly attached to posterior surface 13. Such an outer surface may be formed from porous material that is able to absorb and retain fluid and debris, for example. The outer surface 14 has a plurality of female protrusions 20 extending outwardly therefrom wherein the skin cleansing agent 22 is housed within the female protrusions 20. A protective layer 15 is also provided and has a plurality of male protrusions 21 extending outwardly therefrom. The protective layer 15 may be a peel away layer (i.e., adhesive affixed wax paper layer) that shields the outer surface 14 and skin cleansing agent 22 during non-use conditions.

In a non-limiting exemplary embodiment, when the protective layer 15 is affixed to the outer surface 14 of the body 30, the male protrusions 21 are interfitted within the female protrusions 20 thereby maintaining the skin cleansing agent 22 compartmentalized entirely within the female protrusions 20. This configuration ensures the skin cleansing agent 14 does not prematurely dehydrate prior to use of finger sleeve 10.

In a non-limiting exemplary embodiment, when the protective layer 15 is removed from the outer surface 14 of the body 30, the male protrusions 21 are detached from the female protrusions 20 thereby causing the skin cleansing agent 22 to egress outwardly from the female protrusions 20 and spread along the outer surface 14 of the body 30. Advantageously, separation of the protective layer 15 disengages the male protrusions 21 and bursts the female protrusions 20 such that skin cleansing agent is caused to flow outwardly therefrom. As an example, the male protrusions 21 may be initially positioned within the female protrusions 20. Thereafter, the skin cleansing agent 22 may be injected into the female protrusions 20 via a syringe or the like. The open area of the female protrusion 20 may be heat sealed or otherwise blocked off in a manner that permits extraction of the male protrusions 21 therefrom as the protective layer 15 is peeled away from the outer surface 14.

In a non-limiting exemplary embodiment, the cleansing agent 22 includes a liquid hypo-allergenic solution.

In a non-limiting exemplary embodiment, the female protrusions 20 include spherical sockets and the male protrusions 21 include spherical balls or tear drop shaped members (e.g., FIGS. 2 and 3).

In a non-limiting exemplary embodiment, a jar (not shown but well understand by one skilled in the art) is provided which contains the cleansing agent 22 therein.

In a non-limiting exemplary embodiment, the outer surface 14 is smooth and the cleansing agent 22 is disposed along the outer surface 14 of the finger sleeve 10.

The disclosure further includes a method of utilizing a skin cleansing finger sleeve 10. Such a method includes the chronological steps of: providing an elongated body 30 formed from water impermeable material wherein the body 30 has an open proximal end 32 and a closed distal end 33; providing and applying a viscous skin cleansing agent 22 to the body 30 for treating the user skin; removably positioning the body 30 about a user finger 31; and the finger sleeve 10 cleaning a user face by applying the skin cleansing agent 22 to the user face and removing facial makeup.

In a non-limiting exemplary embodiment, the apparatus of this invention is referred to generally in the figures and is intended to provide a disposable skin cleansing finger sleeve 10 containing a cleansing solution for cleaning pores, as well as eliminating blackheads and acne. It should be understood that the present invention may be used to clean many different types of skin textures, and should not be limited to any particular skin texture described herein. Also for removing make up and applying medicine, maintain a clean face.

In a non-limiting exemplary embodiment, a specially designed fitted sleeve 10 may include a body 30 adapted to be worn over the index finger 31 and utilized in conjunction with a gentle cleansing solution 22 formulated to clean facial pores. Generally tubular in shape and closed at its distal end 33, the finger sleeve 10 may be a fitted sheath designed to completely encompass the index finger 31, extending down to the user's first knuckle, for example. Disposable, the finger sleeve 10 could be manufactured of water impermeable material, wherein an outer surface 14 can be formed from a sanitary paper or natural or synthetic cotton material, tightly woven to ensure a snug and secure fit. The finger sleeve 10 can be used as a dry application device or moistened product. The finger sleeve 10 can be a raised, textured model, or a smooth surface model.

In a non-limiting exemplary embodiment, an outer surface 14 of the finger sleeve 10 may feature a coarse and slightly abrasive texture designed to deeply clean, and/or exfoliate pores, eradicating blackheads and pimples on contact. For practical purposes, the finger sleeve 10 could be wrapped in sterile packaging.

In a non-limiting exemplary embodiment, a skin cleansing agent 22 may be formed as a liquid to cleanse skin pores. Such a skin cleansing agent 22 may be a hypo-allergenic solution safe for all skin types and boasting disinfecting properties. To facilitate ease of use, the skin cleansing agent 22 could be packaged in a handy, lidded jar, enabling the user to literally dip their sheathed finger sleeve 10 within the skin cleansing agent 22 in order to saturate the finger sleeve 10 prior to cleaning their face, or package in a pair of 24 finger sleeve, already moist in a cleaning formula for easy use.

In a non-limiting exemplary embodiment, the finger sleeve 10 could be packaged with existing conventional cleansing solutions such as AVEENO®, NEUTROGENA®, and/or OLAY®, to name a few options.

In a non-limiting exemplary embodiment, the finger sleeve 10 may be sold in a set of 24 finger sleeves, per container, and already moist with solution for easy use or in a set containing a plurality of disposable sleeves and a jar of the skin cleansing agent 22.

In a non-limiting exemplary embodiment, use of the finger sleeve 10 is straight forward. First, the user may remove a single finger sleeve 10 from the product packaging, sliding the sleeve over their dominant index finger and making any necessary adjustments for a comfortable fit. Next, the user may open the cleaning agent jar, and thereafter dip the sheathed finger sleeve 10 directly therein. When the finger sleeve 10 has been saturated with the skin cleansing agent 22, the user may apply the cleansing agent to the face, via the finger sleeve 10. Gently massaging the saturated finger sleeve 10 into the skin, the user may buff away blackheads and pimples, simultaneously depositing the disinfecting formula into the pores, thus preventing new acne from forming.

The user might also choose to employ two finger sleeves 10, one on either index finger in order to further facilitate the application process, as well as to enjoy a truly pampering treatment or as another option the user might buy already packaged moist finger sleeve product for everyday use. After use, the finger sleeve 10 may be removed and discarded in the nearest trash receptacle. The user may then secure the lid to the skin cleansing agent 22, storing the finger sleeve container away until again needed or use already moist finger sleeves with solution. The finger sleeve 10 provides an exceptional way to cleanse the face, remove make up, and serves as a device in application of medicine.

While non-limiting exemplary embodiment(s) has/have been described with respect to certain specific embodiment(s), it will be appreciated that many modifications and changes may be made by those of ordinary skill in the relevant art(s) without departing from the true spirit and scope of the present disclosure. It is intended, therefore, by the appended claims to cover all such modifications and changes that fall within the true spirit and scope of the present disclosure. In particular, with respect to the above description, it is to be realized that the optimum dimensional relationships for the parts of the non-limiting exemplary embodiment(s) may include variations in size, materials, shape, form, function and manner of operation.

The Abstract of the Disclosure is provided to comply with 37 C.F.R. §1.72(b) and is submitted with the understanding that it will not be used to interpret or limit the scope or meaning of the claims. In addition, in the above Detailed Description, various features may have been grouped together or described in a single embodiment for the purpose of streamlining the disclosure. This disclosure is not to be interpreted as reflecting an intention that the claimed embodiment(s) require more features than are expressly recited in each claim. Rather, as the following claims reflect, inventive subject matter may be directed to less than all of the features of any of the disclosed non-limiting exemplary embodiment(s). Thus, the following claims are incorporated into the Detailed Description, with each claim standing on its own as defining separately claimed subject matter.

The above disclosed subject matter is to be considered illustrative, and not restrictive, and the appended claims are intended to cover all such modifications, enhancements, and other embodiment(s) which fall within the true spirit and scope of the present disclosure. Thus, to the maximum extent allowed by law, the scope of the present disclosure is to be determined by the broadest permissible interpretation of the following claims and their equivalents, and shall not be restricted or limited by the above detailed description.

What is claimed as new and what is desired to secure by Letters Patent of the United States is:

1. A skin cleansing finger sleeve comprising:
   an elongated body having an open proximal end and a closed distal end capable of being removably positioned about a user finger; and
   a skin cleansing agent applied to said body for treating the user skin;
   wherein said finger sleeve is capable of cleaning a user face by applying said skin cleansing agent to the user face and removing facial makeup therefrom;
   wherein said body comprises
      an outer surface having a plurality of female protrusions extending outwardly therefrom, said skin cleansing agent being housed within said female protrusions, and
      a protective layer having a plurality of male protrusions extending outwardly therefrom;
      wherein said outer surface is abrasive;
   wherein, when said protective layer is affixed to said outer surface of said body, said male protrusions are interfitted within said female protrusions thereby maintaining said skin cleansing agent compartmentalized entirely within said female protrusions.

2. The skin cleansing finger sleeve of claim 1, wherein, when said protective layer is removed from said outer surface of said body, said male protrusions are detached from said female protrusions thereby causing said skin cleansing agent to egress outwardly from said female protrusions and spread along said outer surface of said body.

3. The skin cleansing finger sleeve of claim 2, wherein said cleansing agent comprises: a liquid hypo-allergenic solution.

4. The skin cleansing finger sleeve of claim 3, wherein said female protrusions comprise spherical sockets and said male protrusions comprise spherical balls.

5. The skin cleansing finger sleeve of claim 4, wherein said outer surface is smooth and said cleansing agent is disposed along said outer surface of said finger sleeve.

6. A skin cleansing finger sleeve comprising:
   an elongated body formed from water impermeable material, said body having an open proximal end and a closed distal end capable of being removably positioned about a user finger; and
   a viscous skin cleansing agent applied to said body for treating the user skin;
   wherein said finger sleeve is capable of cleaning a user face by applying said skin cleansing agent to the user face and removing facial makeup therefrom;
   wherein said body comprises
      an outer surface having a plurality of female protrusions extending outwardly therefrom, said skin cleansing agent being housed within said female protrusions, and
      a protective layer having a plurality of male protrusions extending outwardly therefrom;
      wherein said outer surface is abrasive;
   wherein, when said protective layer is affixed to said outer surface of said body, said male protrusions are interfitted within said female protrusions thereby maintaining said skin cleansing agent compartmentalized entirely within said female protrusions.

7. The skin cleansing finger sleeve of claim 6, wherein, when said protective layer is removed from said outer surface of said body, said male protrusions are detached from said female protrusions thereby causing said skin cleansing agent to egress outwardly from said female protrusions and spread along said outer surface of said body.

8. The skin cleansing finger sleeve of claim 7, wherein said cleansing agent comprises: a liquid hypo-allergenic solution.

9. The skin cleansing finger sleeve of claim 8, wherein said female protrusions comprise spherical sockets and said male protrusions comprise spherical balls.

10. The skin cleansing finger sleeve of claim 9, wherein said outer surface is smooth and said cleansing agent is disposed along said outer surface of said finger sleeve.

11. A method of utilizing a skin cleansing finger sleeve, said method comprising the steps of:
   providing an elongated body formed from water impermeable material, said body having an open proximal end and a closed distal end;
   providing and applying a viscous skin cleansing agent to said body for treating the user skin;
   removably positioning said body about a user finger; and
   said finger sleeve cleaning a user face by applying said skin cleansing agent to the user face and removing facial makeup;
   wherein said body comprises
      an outer surface having a plurality of female protrusions extending outwardly therefrom, said skin cleansing agent being housed within said female protrusions, and
      a protective layer having a plurality of male protrusions extending outwardly therefrom;
      wherein said outer surface is abrasive;
   wherein, when said protective layer is affixed to said outer surface of said body, said male protrusions are interfitted within said female protrusions thereby maintaining said skin cleansing agent compartmentalized entirely within said female protrusions.

* * * * *